United States Patent
Gaines et al.

(10) Patent No.: US 9,649,432 B2
(45) Date of Patent: May 16, 2017

(54) CERTIFICATION CASSETTE AND RELATED METHODS

(71) Applicant: Covidien LP, Mansfield, MA (US)

(72) Inventors: Robert Gaines, Lake Saint Louis, MO (US); John Holste, Hamburg, IL (US); Christopher Knauper, St. Charles, MO (US); Joel Wiesner, St. Peters, MO (US)

(73) Assignee: Covidien LP, Mansfield, MA (US)

( * ) Notice: Subject to any disclaimer, the term of this patent is extended or adjusted under 35 U.S.C. 154(b) by 253 days.

(21) Appl. No.: 14/501,444

(22) Filed: Sep. 30, 2014

(65) Prior Publication Data

US 2015/0093307 A1    Apr. 2, 2015

Related U.S. Application Data

(60) Provisional application No. 61/884,665, filed on Sep. 30, 2013.

(51) Int. Cl.
*A61M 5/142* (2006.01)
*F04B 43/12* (2006.01)
*F04B 51/00* (2006.01)

(52) U.S. Cl.
CPC ........ *A61M 5/142* (2013.01); *A61M 5/14232* (2013.01); *F04B 43/1261* (2013.01);
(Continued)

(58) Field of Classification Search
CPC .... A61M 5/14232; A61M 2005/16863; A61M 2005/16868; A61M 2005/16872;
(Continued)

(56) References Cited

U.S. PATENT DOCUMENTS

2001/0020148 A1    9/2001    Sasse et al.
2005/0267439 A1    12/2005    Harr et al.
(Continued)

FOREIGN PATENT DOCUMENTS

WO    2014077940 A1    5/2014

OTHER PUBLICATIONS

International Preliminary Report on Patentability dated Sep. 24, 2015 in related International Application No. PCT/US2014/058201, 6 pages.

(Continued)

*Primary Examiner* — Blake A Tankersley
(74) *Attorney, Agent, or Firm* — Blaine A. Page, Esq.

(57) ABSTRACT

A certification cassette for testing a pumping apparatus including at least one identification reader. The cassette comprises a housing configured for releasable attachment to the pumping apparatus in an aligned position. A space defined within the housing is configured to receive a rotor of the pumping apparatus therein when the housing is in the aligned position. The space is free of fluid carrying conduits disposed for engaging the rotor. An identification member is positioned in the housing. The identification member is operable to induce an expected identification reader response when the identification reader is functioning properly. The cassette is arranged to operatively align the identification member with the identification reader when the housing is in the aligned position.

16 Claims, 10 Drawing Sheets

(52) U.S. Cl.
CPC ......... *F04B 51/00* (2013.01); *A61M 2205/12* (2013.01); *A61M 2205/3317* (2013.01); *A61M 2205/3375* (2013.01); *A61M 2205/60* (2013.01); *A61M 2205/6054* (2013.01); *A61M 2205/70* (2013.01); *A61M 2209/02* (2013.01)

(58) Field of Classification Search
CPC ...... A61M 2205/60; A61M 2205/6054; A61M 2205/6018; A61M 2205/70; A61M 2205/12; A61M 2205/3375; A61M 2209/02; F04B 43/1253; F04B 43/1276; F04B 43/1261; F04B 43/1238; F04B 51/00
See application file for complete search history.

(56) References Cited

U.S. PATENT DOCUMENTS

2012/0083735 A1* 4/2012 Pfouts ............... A61M 5/14232
604/151
2013/0002102 A1* 1/2013 Chen ..................... G06F 1/1656
312/223.1
2013/0071272 A1* 3/2013 Juretich .............. F04B 43/1261
417/477.2

OTHER PUBLICATIONS

International Search Report and Written Opinion dated Dec. 22, 2014 in related International application PCT/US2014/058201, 9 pages.
Patent Examination Report No. 1 dated Sep. 26, 2016 in related Australian Application No. 2014324552, 4 pages.
Office Action dated Nov. 28, 2016 in related Chinese Application No. 201480053900.0, 13 pages.
Office Action dated Jan. 9, 2017 in related Canadian Application No. 2925569, 3 pages.
Office Action dated Feb. 6, 2017 in related European Application No. 14790842.0, 4 pages.

* cited by examiner

CERTIFICATION CASSETTE AND RELATED METHODS

CROSS-REFERENCE TO RELATED APPLICATION

The present application claims the benefit of U.S. Patent Application Ser. No. 61/884,665, entitled Certification Cassette, filed Sep. 30, 2013, the complete disclosure of which is incorporated herein by reference for all purposes.

BACKGROUND

Field

The present invention generally relates to a certification system for a pumping apparatus, and more particularly, to a certification cassette for verifying that certain components of a pumping apparatus are functioning properly, within a predetermined operational range.

Related Art

Pumping apparatuses are frequently used to deliver nutritional and medicinal fluids to patients. It may be important to ensure consistent and accurate delivery of these fluids for the health and safety of the patient. Accordingly, pumping apparatuses may be certified on an occasional or more frequent schedule. During certification, components of the pumping apparatus are tested to verify that they are functioning properly, within a predetermined operational range. Prior art certification systems may require a user of a pumping apparatus to use precisely measured volumes of fluids. These systems may be cumbersome or onerous to a home user of a pumping apparatus, or even a professional user.

SUMMARY

In one aspect, the present invention includes a certification cassette for testing a pumping apparatus including at least one identification reader. The cassette comprises a housing configured for releasable attachment to the pumping apparatus in an aligned position. A space defined within the housing is configured to receive a rotor of the pumping apparatus therein when the housing is in the aligned position. The space is free of fluid carrying conduits disposed for engaging the rotor. An identification member is positioned in the housing. The identification member is operable to induce an expected identification reader response when the identification reader is functioning properly. The cassette is arranged to operatively align the identification member with the identification reader when the housing is in the aligned position.

In some embodiments, the identification member comprises identification member components disposed in different places on the housing.

In certain embodiments, there is one distinct identification member component for each identification reader of the pumping apparatus.

In some embodiments the identification member comprises a magnetic material.

In some embodiments, the identification member comprises a magnetically-susceptible metallic material.

In some embodiments, the identification member is configured to induce an expected Hall-effect sensor response when the identification reader is functioning properly.

In some embodiments, certification cassette further comprises an ultrasonic wave-transmissive body supported by the housing. The body is configured to induce an expected ultrasonic sensor response when an ultrasonic sensor of the pumping apparatus is functioning properly.

In certain embodiments, the cassette is configured to align the body with the ultrasonic sensor when the housing is in the aligned position.

In another aspect, a method of facilitating certification of a pumping apparatus, comprises providing a certification cassette for testing a pumping apparatus, wherein the cassette has a housing configured for releasable attachment to the pumping apparatus in an aligned position; a space defined by the housing and configured to receive a rotor of the pumping apparatus therein when the housing is in the aligned position, wherein the space is free of fluid carrying conduits disposed for engaging the rotor; and a body comprising an ultrasonic wave-transmissive material positioned in the housing, wherein the body is configured to induce an expected ultrasonic sensor response when the ultrasonic sensor is functioning properly, and wherein the cassette is arranged to align the body with the ultrasonic sensor when the housing is in the aligned position.

In some embodiments, the cassette can further comprise an identification member positioned in the housing, the identification member operable to induce an expected identification reader response from an identification reader of the pumping apparatus when the identification reader is functioning properly, wherein the cassette is arranged to operatively align the identification member with the identification reader when the housing is in the aligned position.

In another aspect, the present invention includes a certification cassette for testing a pumping apparatus. The cassette comprises a housing configured for releasable attachment to the pumping apparatus in an aligned position. A space defined by the housing is configured to receive a rotor of the pumping apparatus therein when the housing is in the aligned position. The space is free of fluid carrying conduits disposed for engaging the rotor. A body comprising an ultrasonic wave-transmissive material is positioned in the housing. The body is configured to induce an expected ultrasonic sensor response when the ultrasonic sensor is functioning properly. The cassette is arranged to align the body with the ultrasonic sensor when the housing is in the aligned position.

In some embodiments, the ultrasonic wave-transmissive material has a density greater than air.

In certain embodiments, the ultrasonic wave-transmissive material has a density corresponding to liquid.

In certain embodiments, the ultrasonic wave-transmissive material comprises silicone.

In some embodiments, the body comprises a post having a cylindrical shape.

In some embodiments, the body is free of liquid.

In some embodiments, the certification cassette comprises an identification member positioned in the housing. The identification member is operable to induce an expected identification reader response from an identification reader of the pumping apparatus when the identification reader is functioning properly.

In certain embodiments, the cassette is arranged to operatively align the identification member with the identification reader when the housing is in the aligned position.

Other aspects and embodiments of the present invention will be apparent in view of the following description and claims.

BRIEF DESCRIPTION OF THE DRAWINGS

Corresponding reference characters indicate corresponding parts throughout the drawings.

DETAILED DESCRIPTION

Figure 1:
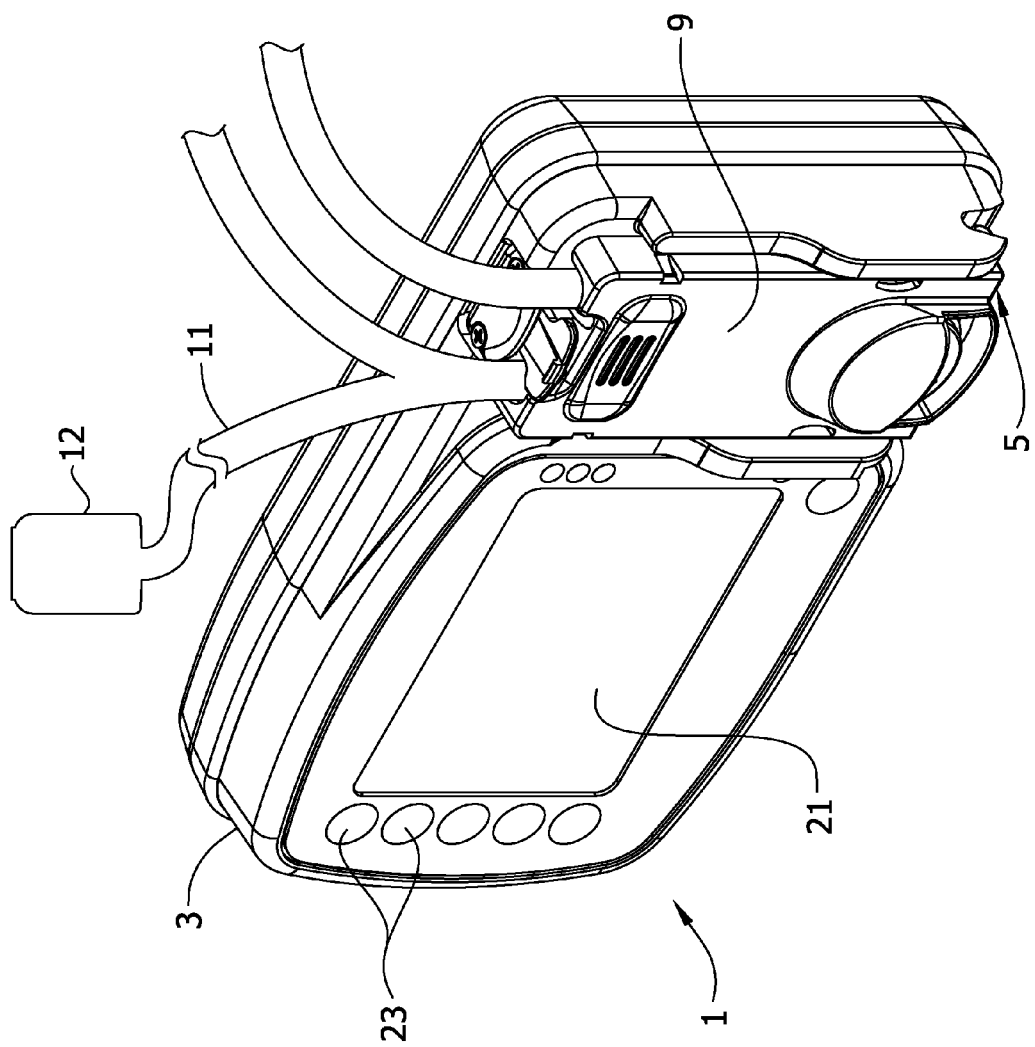
FIG. 1 is a schematic illustration showing a perspective view of a pumping apparatus and a fragmentary portion of a feeding set (illustrated schematically) received on the pumping apparatus.
Figure 2:
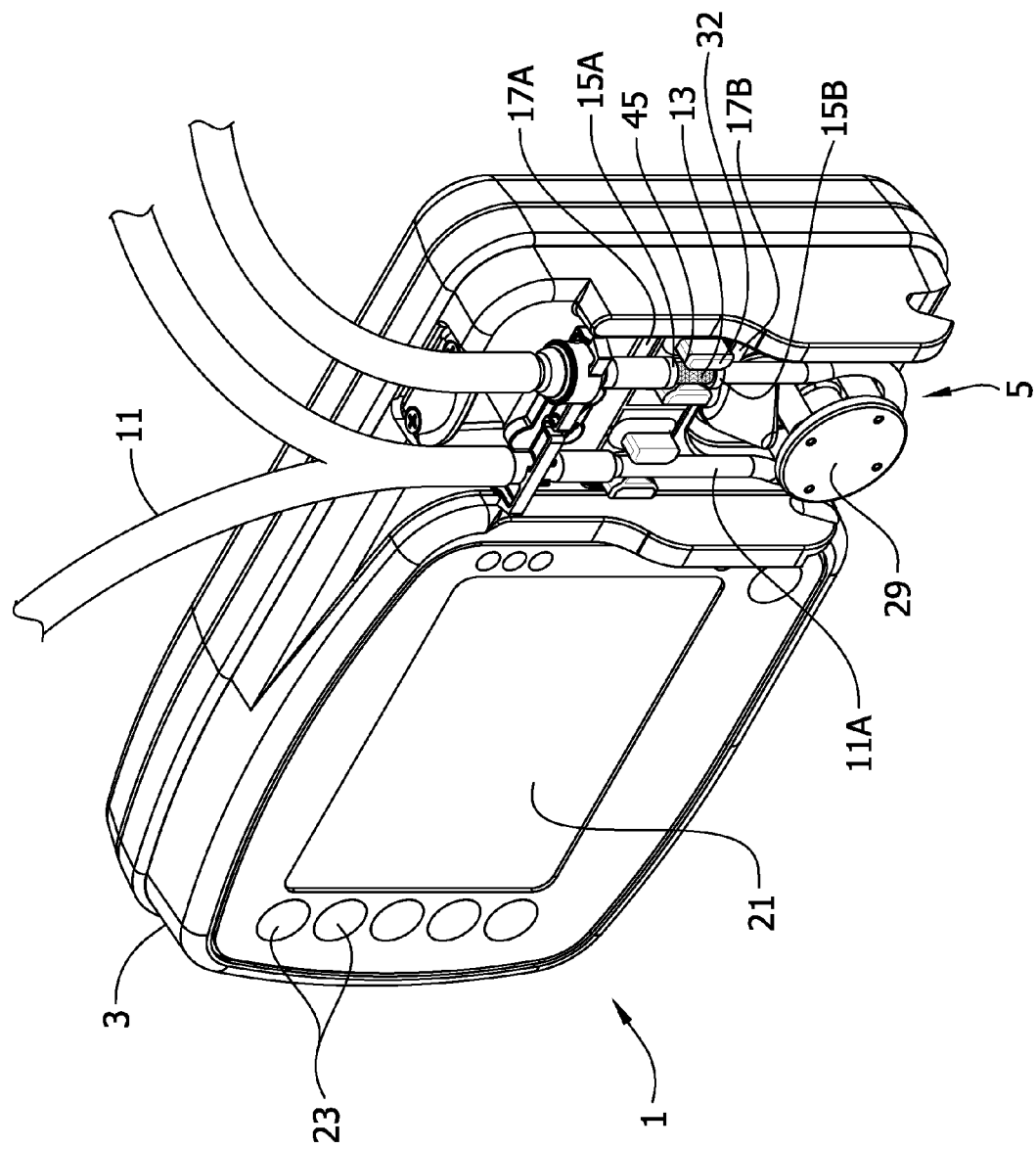
FIG. 2 is a schematic illustration showing the perspective view of FIG. 1 with a cassette housing of the feeding set removed.
Figure 3:
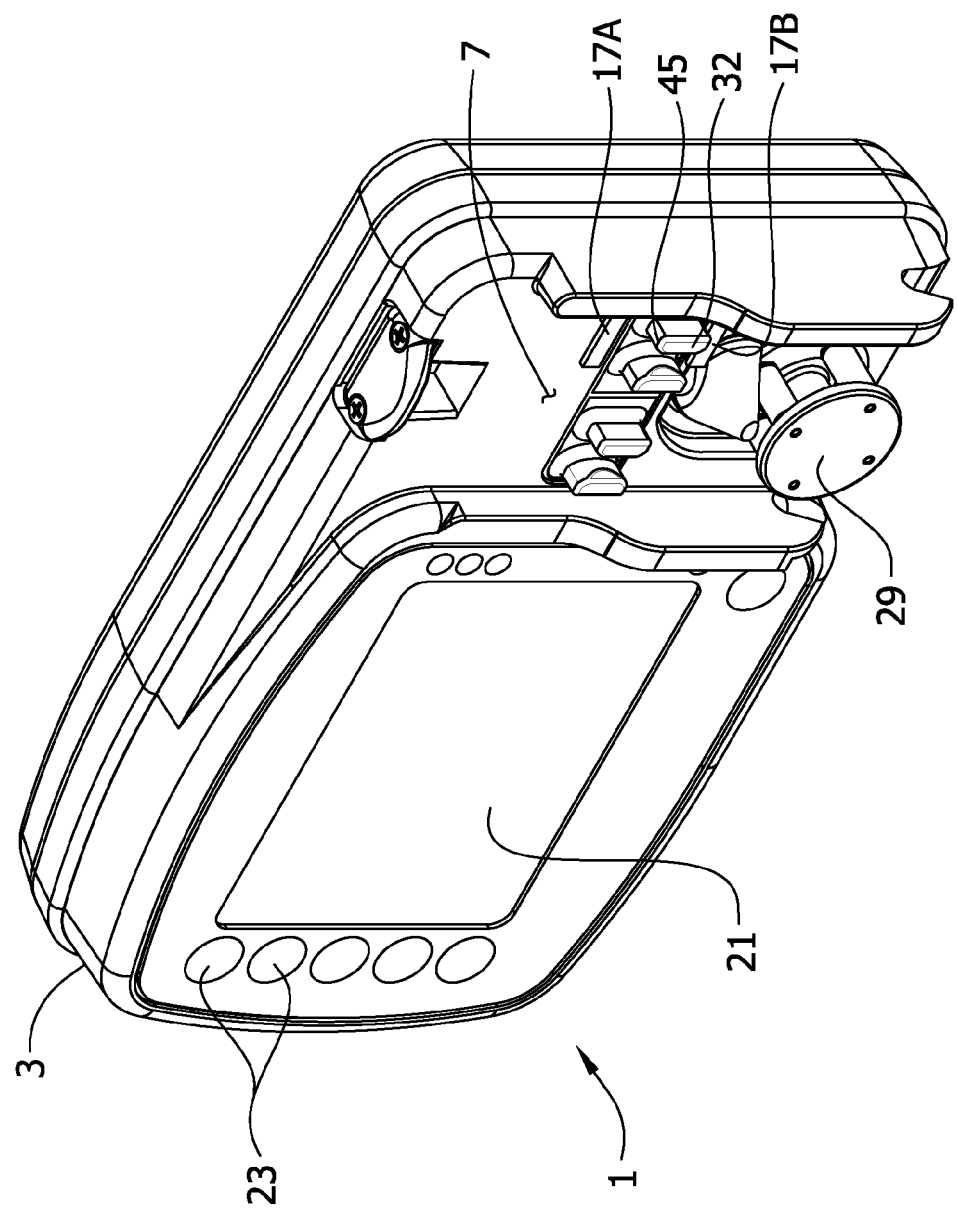
FIG. 3 is a schematic illustration showing the perspective view of FIG. 1 with the feeding set removed.

Referring to FIGS. 1-2, an embodiment of a pumping apparatus configured for certification according to the principles of the present invention is generally indicated at 1. In the illustrated embodiment, the pumping apparatus 1 is shown with a feeding set installed, generally indicated at 5. The pumping apparatus 1 is configured for operable connection to a certification cassette (not shown in FIGS. 1 and 2) to verify that at least one component of the pumping apparatus is functioning within a predetermined operational range. The certification set will be described in more detail hereinafter. As will be understood, when the feeding set 5 is loaded into the pumping apparatus 1, it is suitable for delivering nutrients and/or medication to a patient. The pumping apparatus 1 does not need to deliver nutrients or medication while certification is carried out. In some embodiments, the certification cassette can be free of any fluid carrying conduits. The certification cassette of the present invention may function to verify that certain components of the pumping apparatus 1 are functioning properly, e.g., within a predetermined operational range. The term certification should be understood to include any such verification, whether performed at a manufacturing facility of the pumping apparatus 1 or at its site of use, e.g., at a user's or patient's home or hospital. The term certification should broadly be understood to include all certifications or re-certifications that may be performed in the art.

The following description illustrates the components of the pumping apparatus 1 when a feeding set 5 is loaded and used thereon. Though reference will be made to one embodiment of a pumping apparatus, it should be understood that other embodiments may also be subject to certification according to the principles discussed herein without departing from the scope of the invention.

Referring to FIGS. 1-4, the pumping apparatus 1 includes a pump housing 3 defining a recess 7 that can receive portions of the feeding set 5. A display 21 and suitable buttons 23 for operating the pumping apparatus are in the housing. Internally, the pump housing 3 contains a motor 28 (FIG. 4) that drives a rotor 29 projecting from the housing.

Pump electronics of the pumping apparatus 1 include, for example, identification readers 17A, 17B, the display 21, the motor 28 and an ultrasonic sensor 32. A microprocessor 38 in the pump housing 3 controls the pump electronics and uses a memory 39. A software subsystem 36 is shown schematically separate from the memory 39, and includes a flow monitoring system 36A, a set identification system 36B capable of identifying the type of set mounted on the pumping apparatus 1, and a certification system 36C, the operations of which will be described more fully hereinafter.

The illustrated feeding set 5 may include tubing 11 that can be loaded on the pumping apparatus 1 for delivery of fluid to a patient. As used herein, the term load means arranging a section 11A of the tubing 11 around a rotor 29 of the pumping apparatus 1 so when the rotor is turning fluid contained in the tubing may be transported therethrough by peristaltic action. The pumping apparatus 1 may comprise a pump housing 3 adapted for loading the feeding set 5 on the pumping apparatus. In use, the tubing 11 of the feeding set 5 provides a fluidic pathway between a bag 12 of nutritional or medicinal liquid and a patient. The bag 12 is shown schematically in FIG. 1. An upstream portion of the tubing 11 carries fluid toward the rotor 29, while a downstream portion carries fluid away from the rotor. In the illustrated embodiment, a portion of the tubing 11 is mounted in a feeding cassette 9.

The feeding cassette 9 may be installed in a recess 7 (FIG. 3) of the pump housing 3 to load the tubing 11 on the pumping apparatus 1. The set identification subsystem 36B can identify that a feeding set 5 has been loaded and cause the pumping apparatus to operate in a mode for feeding. The rotor 29, may be rotated by the motor 28 (FIG. 4) and adapted to engage the tubing section 11A. In the illustrated embodiment, the motor 28 and rotor 29 may broadly be considered "a pumping device". It is contemplated that any pumping apparatus having a means for driving fluid may be used, such as a linear peristaltic pump, bellows pump, turbine pump, rotary peristaltic pump, and displacement pump. Rotation of rotor 29 translates a plurality of rollers which compress the tubing 11 and provides a means for driving fluid from the upstream to the downstream side of the feeding set 5 for delivery to a patient.

The motor 28 may draw current from a power source (not shown) to turn the rotor 29. The current draw of the motor 28 may vary with its load. Thus, when a feeding set 5 is loaded on the pumping apparatus 1, the tubing 11, in compressed engagement with the rotor 29, may increase the load on the motor 28. Preferably, a properly functioning motor 28 will draw a consistent current under consistent load conditions, e.g., when no feeding set is loaded.

To detect flow conditions in the downstream portion of the tubing 11, the ultrasonic sensor 32 is configured for alignment with the downstream portion of the tubing 11. In the illustrated embodiment, the sensor 32 is positioned in the recess 7 and is adapted to receive the tubing 11 therein when the feeding set 5 is loaded on the pumping apparatus 1. The ultrasonic sensor 32 may be configured to produce a signal representative of the pressure buildup (or fluid flow) in the downstream portion of the tubing 11. In combination with the microprocessor 38 and the flow monitoring subsystem 36A of software subsystem 36, the ultrasonic sensor 32 may be configured to alert to an undesirable flow condition in the downstream portion of the tubing 11. Such an alert may be presented to a user on the display 21. Though sensor 32 is described above as an ultrasonic sensor, it should be noted that other suitable flow condition sensors may also be used in combination with the certification cassette discussed below without departing from the scope of the invention. Moreover, though the illustrated pumping apparatus 1 only includes a first, downstream ultrasonic sensor 32, it is also contemplated that a second, upstream ultrasonic sensor may be used.

As shown best in FIG. 2, a mounting member 13 is configured to engage a mount 45 of the pumping apparatus 1 when the feeding set 5 is loaded thereon. Readers 17A, 17B disposed on or within the pumping apparatus 1, may detect the presence of respective identification members 15A, 15B attached to the feeding set 5. Preferably, the identification members 15A, 15B may be configured to be aligned with respective ones of the readers 17A, 17B when the feeding set 5 is loaded on the pumping apparatus 1. Although first and second identification members 15A, 15B and first and second readers 17A, 17B are shown, any number of identification components may be employed. The identification members 15A, 15B may be magnetic components or, in the alternative, magnetically-susceptible metallic components capable of detection by readers 17A, 17B, respectively without requiring direct physical contact with the reader. The readers 17A, 17B may be Hall-effect sensors or other types of proximity sensors that are positioned near the mount 45 such that the readers 17A, 17B can detect the presence of the identification members 15A, 15B when the mounting member 13 is engaged in the mount 45. Other types of readers may also be used.

Upon engagement of the mounting member 13 to the mount 45, readers 17A, 17B may be capable of sensing the identification data represented by the number and position of the identification members 15A, 15B. In combination with the microprocessor 38, memory 39, and software subsystem 36, the readers 17A, 17B and the identification members 15A, 15B may identify at least one characteristic of the nutritional liquid associated with the feeding set 5 loaded on the pumping apparatus 1. Additionally, they may provide a signal representative of proper alignment when the cassette 9 is properly loaded into the pump housing 3. The set identification subsystem 36B allows the pumping apparatus 1 to identify that a certification set has been loaded, and to configure itself for operating in a configuration mode.

As discussed above, the pumping apparatus 1 includes several electronic features that may be used to ensure consistent and accurate delivery of nutritional or medicinal solutions to patients (e.g., the identification readers 17A, 17B, the ultrasonic sensor 32, and the motor 28). Many of these features should be recertified on occasion for the health and safety of the patient to determine whether the pumping apparatus 1 is functioning within a predetermined operational range.

Figure 5:
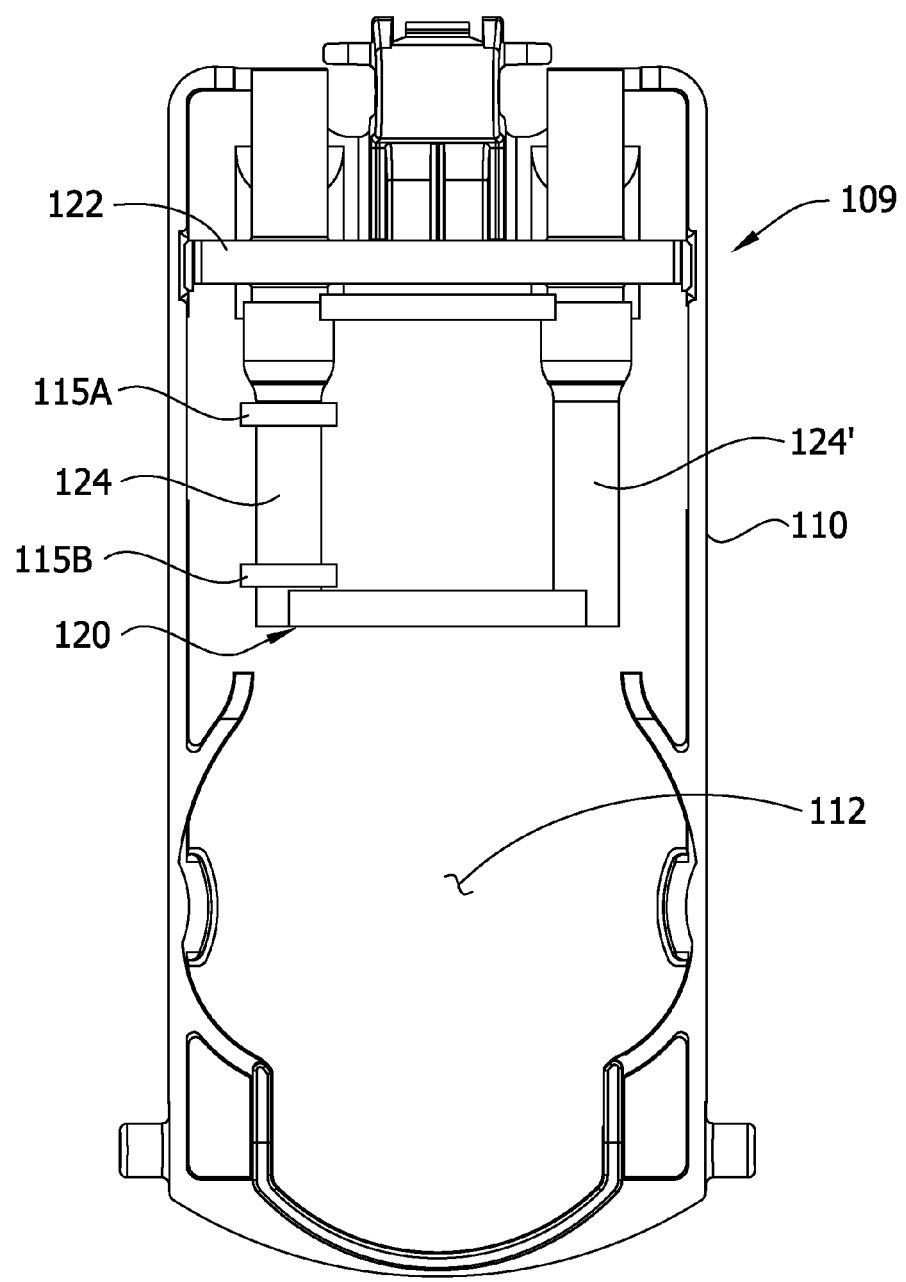
FIG. 5 is a schematic illustration showing a front elevation view of a certification cassette.
Figure 6:
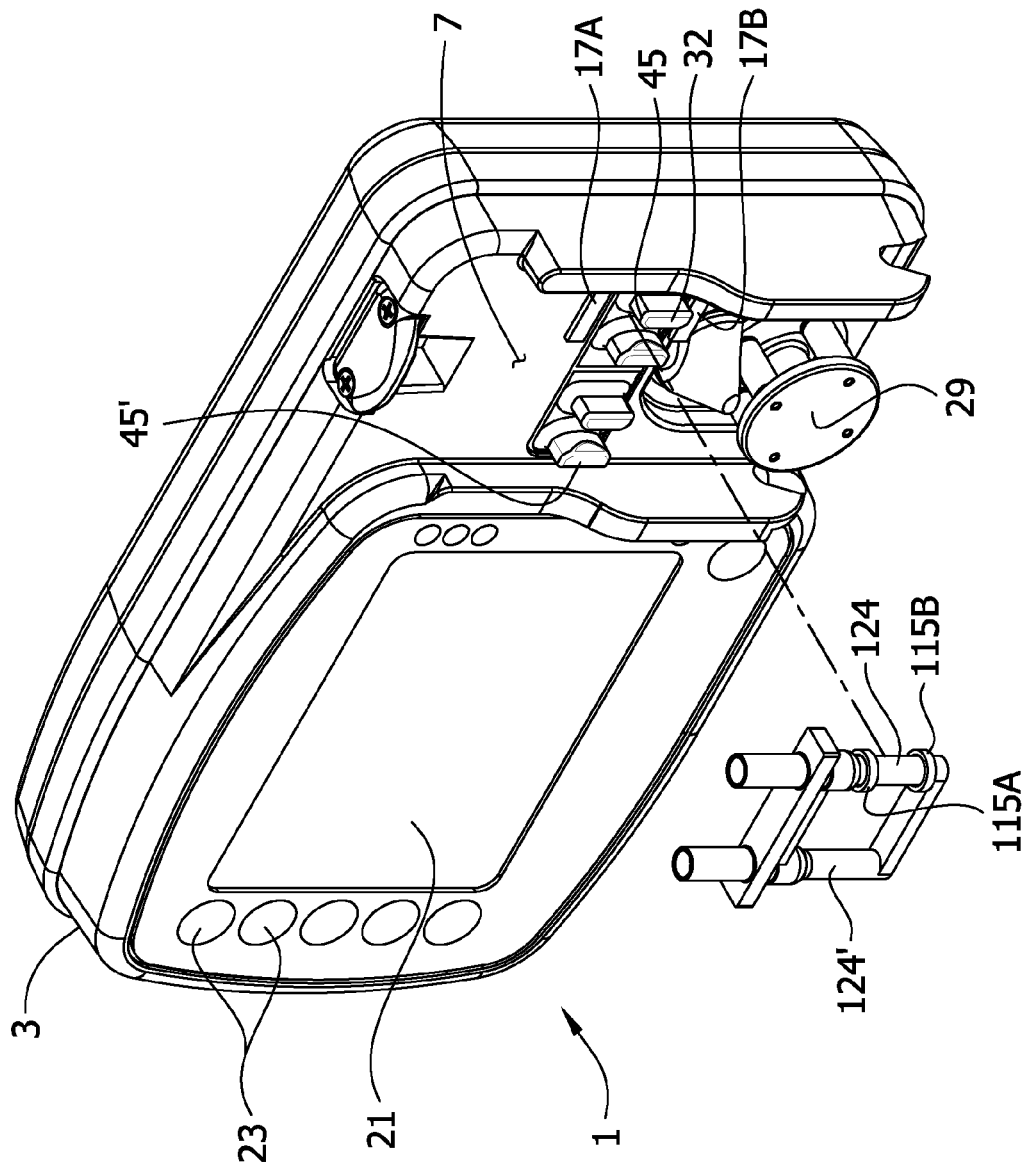
FIG. 6 is the perspective view of FIG. 3 with a sensor body of the certification cassette of FIG. 5 exploded away from the pumping apparatus.
Figure 7:
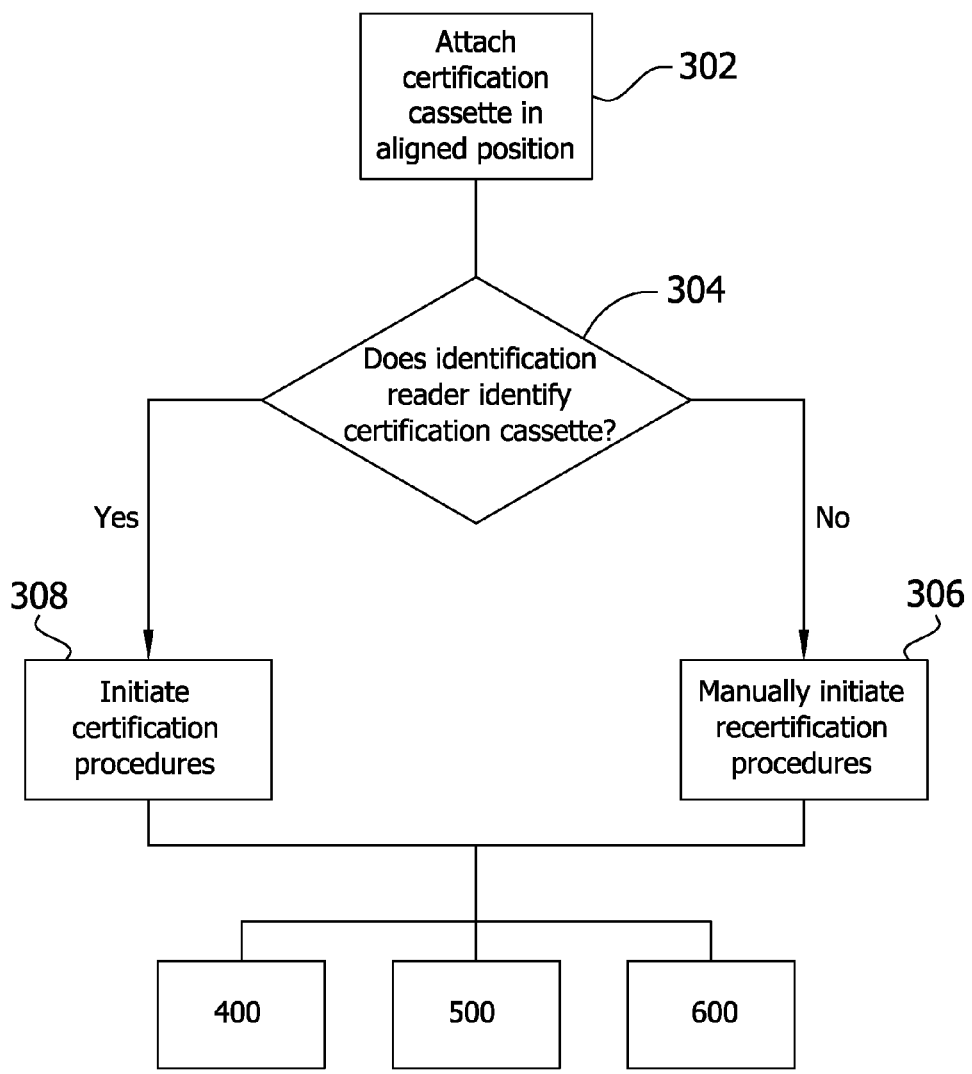
FIG. 7 is a flow chart illustrating the steps and decision points of an initiation routine of the certification system.

Turning now to FIGS. 5-6, a certification cassette for testing a pumping apparatus 1 is indicated generally by reference number 109. The certification cassette 109 includes a housing 110 configured for releasable attachment to the pumping apparatus 1 in an aligned position. More specifically, the illustrated housing 110 is sized to be attachably received in the cavity 7 of the pumping apparatus 1. In some embodiments the housing 110 of the certification cassette 109 may be formed identically to a housing of the feeding cassette 9, shown and discussed above. In this way, manufacturing costs may be minimized. If the housing of the feeding cassette 9 is mass produced through means such as, for example, plastic injection molding, the same molds and tooling may be used to produce the housing 110 of the certification cassette 109. The same is true of any other manufacturing technique used to produce the housing of a feeding cassette 9. However, the housing 110 may be constructed differently from the housing of the feeding cassette 9 without departing from the scope of the present invention.

The housing 110 of the certification cassette 109 may define a space 112. Preferably, the space 112 is free of any fluid carrying conduits disposed for engaging the rotor 29. In some embodiments, the space 112 may be configured to receive a rotor 29 of a pumping apparatus 1 when the housing 110 is in the aligned position. Whereas the feeding cassette 9, discussed above, was configured to engage a fluid carrying tubing 11 with the rotor 29, the certification cassette 109 may be configured such that the space 112 surrounds the rotor 29. Thus, when the housing 110 is attached to the pumping apparatus 1 in the aligned position, the rotor does not engage any fluid carrying conduits. As will be discussed in more detail below, this permits the motor 28 to turn the rotor 29 under repeatable no-load conditions to test the motor's performance and establish a baseline.

As is understood in the art, a properly functioning motor 28 may draw a substantially identical amount of current each time it performs the same operations under the same conditions (e.g., an expected current response). In the illustrated embodiment, the certification cassette 109 is arranged to repeatably configure the motor 28 in substantially identical no-load conditions. The term no-load should be understood to include any built-in motor load, plus the load of the empty rotor 29. Although the illustrated certification cassette 109 is arranged to repeatably configure the motor 28 in substantially identical no-load conditions, it should be understood that other repeatable loading configurations may also be used without departing from the scope of the invention.

In some embodiments, an expected current response may be measured and defined by the peak-to-peak current drawn during a first cycle. In other embodiments, the expected current response may be measured and defined by the average current drawn during a second cycle. In an embodiment discussed in more detail below, a first cycle may be one-eighth of one full rotation of the rotor 29 and a second cycle may be one full rotation of the rotor. However, other cycle lengths and current draw measurements may also be used without departing from the scope of the invention. The expected current response may be determined by calculating or by measuring during a particular pumping apparatus's manufacture. In either case, the expected current response may be stored in the memory 39 of the pumping apparatus 1. Thus, when the housing 110 is in the aligned position, the actual current response may be compared with the expected current response to determine whether the motor 28 is functioning properly (e.g., within a predetermined operational range). Because the certification cassette 109 ensures the motor 28 may be repeatably configured in substantially identical loading conditions, the actual current response of the motor when the housing 110 is in the aligned position should be consistent. A change in actual current response may be an indication that the motor 28 is failing.

In some embodiments, the certification cassette may include identification members 115A, 115B. With respect to the pumping apparatus 1, the cassette 109 is preferably arranged to align the identification members 115A, 115B with respective identification readers 17A, 17B when the housing 110 is in the aligned position (e.g., attached in the cavity 7). The identification members 115A, 115B are disposed in different places on the housing 110. The identification member members 115A, 115B are arranged in the certification cassette 109 to be aligned with the identification readers 17A, 17B when the housing 110 is in the aligned position. Thus, preferably, there can be one distinct identification member for each distinct identification reader. Any number of identification components is envisioned. Preferably, the identification members 115A, 115B may be magnetic components or, in the alternative, magnetically-susceptible metallic components capable of detection by readers 17A, 17B, respectively without requiring direct physical contact with the reader.

Preferably, if the identification readers 17A, 17B are functioning properly, the identification members 115A, 115B are operable to induce an expected identification reader response when the housing 110 is in the aligned position. In certain embodiments, the identification members 115A, 115B are configured to induce an expected Hall-effect sensor response when the identification readers 17A, 17B are functioning properly. The expected identification reader response may be determined by calculating or by measuring during a particular pumping apparatus's manufacture. In either case, the expected identification reader response may be stored in the memory 39 of the pumping apparatus 1. Thus, when the housing 110 is in the aligned position, the actual identification reader response may be compared with the expected identification reader response to determine whether the identification readers 17A, 17B are functioning properly (e.g., within a predetermined operational range). Because the identification members 115A, 115B have known magnetic properties and repeatably align with respective identification readers 17A, 17B when the housing 110 is in the aligned position, the actual response of each reader to the corresponding identification member should be consistent. A change in the actual identification reader response may be an indication that the identification reader (17A or 17B) is failing.

The certification cassette may also include a body 120. In the illustrated embodiment, the body 120 is attached to the cassette housing 110 by way of a body-holding member 122, typically suitably made from thermoplastic material. Moreover, the body 120 may be configured to induce an expected ultrasonic sensor response when the certification cassette 110 is attached to the pumping apparatus 1 in the aligned position and the ultrasonic sensor 32 is functioning properly. The body 120 includes an attachment post 124 configured for attachment to the mount 45 of the pumping apparatus 1. The attachment post 124 preferably attaches to the mount 45 to attach the certification cassette 110 to the pumping apparatus 1 in the aligned position. In the illustrated embodiment, the post 124 has a cylindrical shape. A corresponding attachment post 124' is likewise configured for attachment to a corresponding mount 45'. The post 124 is configured for alignment with the ultrasonic sensor 32 such that the ultrasonic sensor transmits ultrasonic waves through the post and receives ultrasonic waves having been transmitted therethrough. In embodiments where the pumping apparatus 1 includes a second, upstream ultrasonic sensor, the corresponding attachment post 124' may be configured the same way with respect to the second ultrasonic sensor.

In suitable embodiments, the post 124 is formed of an ultrasonic wave-transmissive material with a density greater than air. In certain embodiments, the ultrasonic wave-transmissive material has a density corresponding to liquid even though the body 120 is free of liquid. In some embodiments, the ultrasonic wave-transmissive material may be a silicone material. As will be discussed in more detail below, the post 124 preferably comprises an inert material so that its ultrasonic wave-transmission properties do not change over time. The post 124' can also be made of the same material as the post 124.

The body 120 may be arranged in the certification cassette 109 to repeatably mount the post 124 in the same position with respect to the ultrasonic sensor 32 when the housing 110 is in the aligned position. Thus, a properly functioning ultrasonic sensor 32 may induce an expected ultrasonic sensor response when the housing 110 is in the aligned position. This expected ultrasonic sensor response may be determined by calculating or by establishing at the time of pumping apparatus's manufacture. In either case, the expected ultrasonic sensor response may be stored in the memory 39 of the pumping apparatus 1. Thus, when the housing 110 is in the aligned position, the actual ultrasonic sensor response may be compared with the expected ultrasonic sensor response to determine whether the ultrasonic sensor 32 is functioning properly (e.g., within a predetermined operational range). Because the post 124 is constructed of an inert ultrasonic wave-transmissive material that repeatably aligns with the ultrasonic sensor 32 when the housing 110 is in the aligned position, the actual response of the ultrasonic sensor to the body should be consistent. A change in the actual ultrasonic sensor response may be an indication that the ultrasonic sensor 32 is failing.

Figure 4:
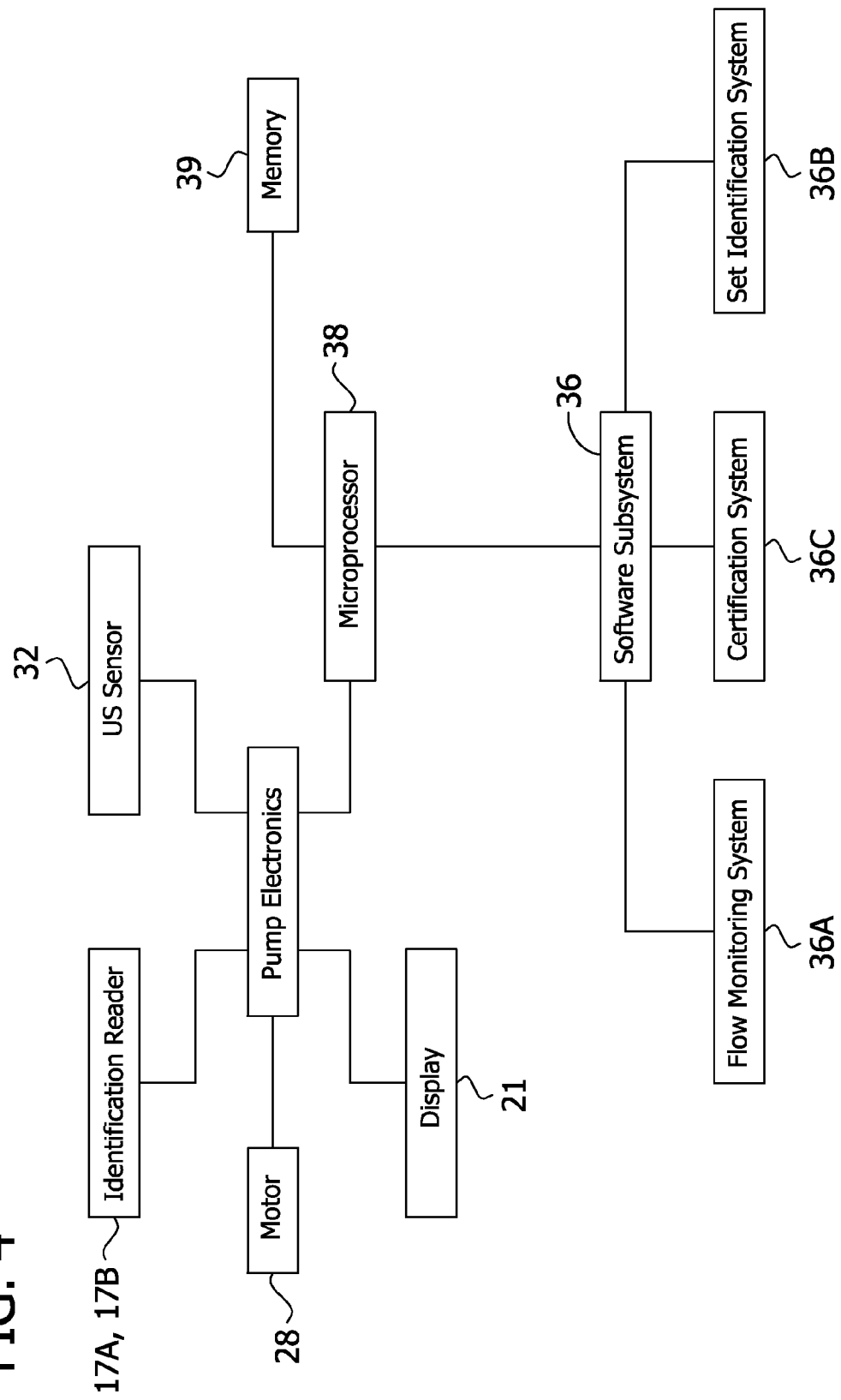
FIG. 4 is block diagram illustrating elements of the pumping apparatus including a certification system.

As shown in FIG. 4, the pumping apparatus 1 may include the software subsystem 36 that performs a certification system 36C in the pumping apparatus when the certification cassette 109 is attached to the pumping apparatus in the aligned position. Certification system 36C determines through a series of decision points and steps whether at least one component of the pumping apparatus 1 is functioning within a predetermined operational range. Referring to the flow charts of FIGS. 7-10, the various decision points and steps executed by the certification system 36C are illustrated.

During an initiation routine 300 (FIG. 7), a user attaches a certification cassette 109 to the pumping apparatus 1 in the aligned position (step 302). As discussed above, when the certification cassette 109 is in the aligned position, the readers 17A, 17B are aligned with respective ones of the certification identification members 115A, 115B to sense the member. At decision point 304, each reader 17A, 17B either identifies or fails to identify the corresponding certification identification member 115A, 115B. If the identification reader 17A, 17B is functioning properly, upon attachment of the certification cassette 109 in the pumping apparatus 1, the initialization routine 300 may automatically direct the pumping apparatus to initiate a certification routine (step 308). Alternatively, if the identification reader 17A, 17B fails to recognize the certification cassette 109 by its identification member 115A, 115B, a user may manually initiate a certification routine using the user input buttons 23 (FIGS. 1-2). Upon initiation of the certification system 36C, the software subsystem may execute any of the routines 400, 500, or 600 discussed in more detail below.

Figure 8:
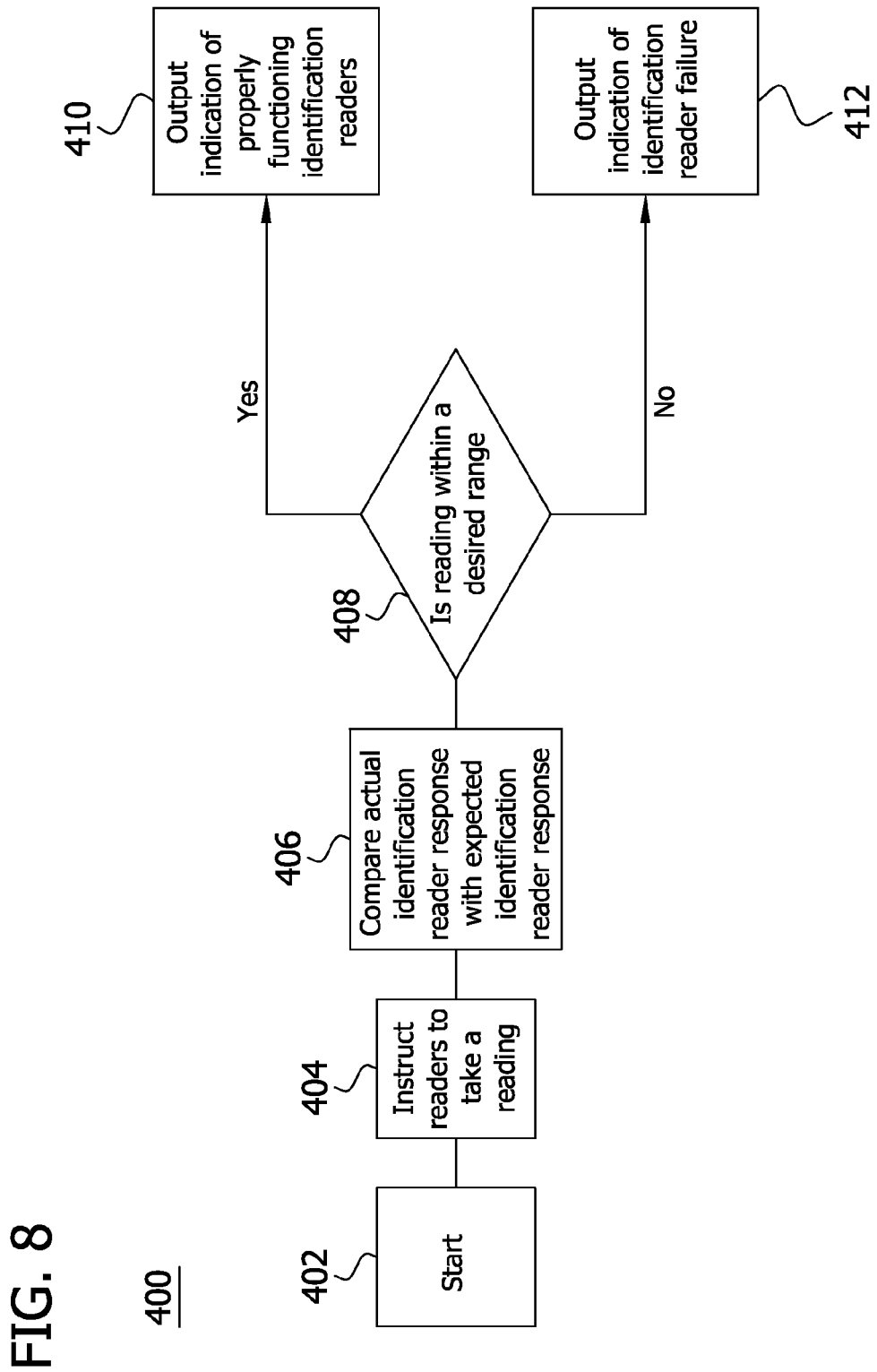
FIG. 8 is a flow chart illustrating the steps and decision points of an identification reader certification routine of the certification system.

Turning now to FIG. 8, the steps and decision points of a routine 400 for determining whether one or more of the identification readers 17A, 17B of the pumping apparatus 1 is functioning within a predetermined operational range may be initiated by routine 300. At step 404, the software subsystem 36 instructs the readers 17A, 17B to take readings. It should be understood that if readers 17A, 17B are always on, step 404 may only require the software subsystem to retrieve a reading. As discussed above, the identification member (115A or 115B) of the certification cassette 109 generates an expected identification reader response from the identification reader (17A or 17B) when the reader is functioning properly. As a result, the measurement taken at step 404 can be compared to the expected identification reader response at step 406 stored in memory 39. If the reading is within a desired range of the expected identification reader response, the software subsystem 36 may output an indication of a properly functioning identification reader on display 21. If the reading is not within a desired range of the expected identification reader response, the software subsystem 36 may output an indication of an improperly functioning identification reader on display 21.

Figure 9:
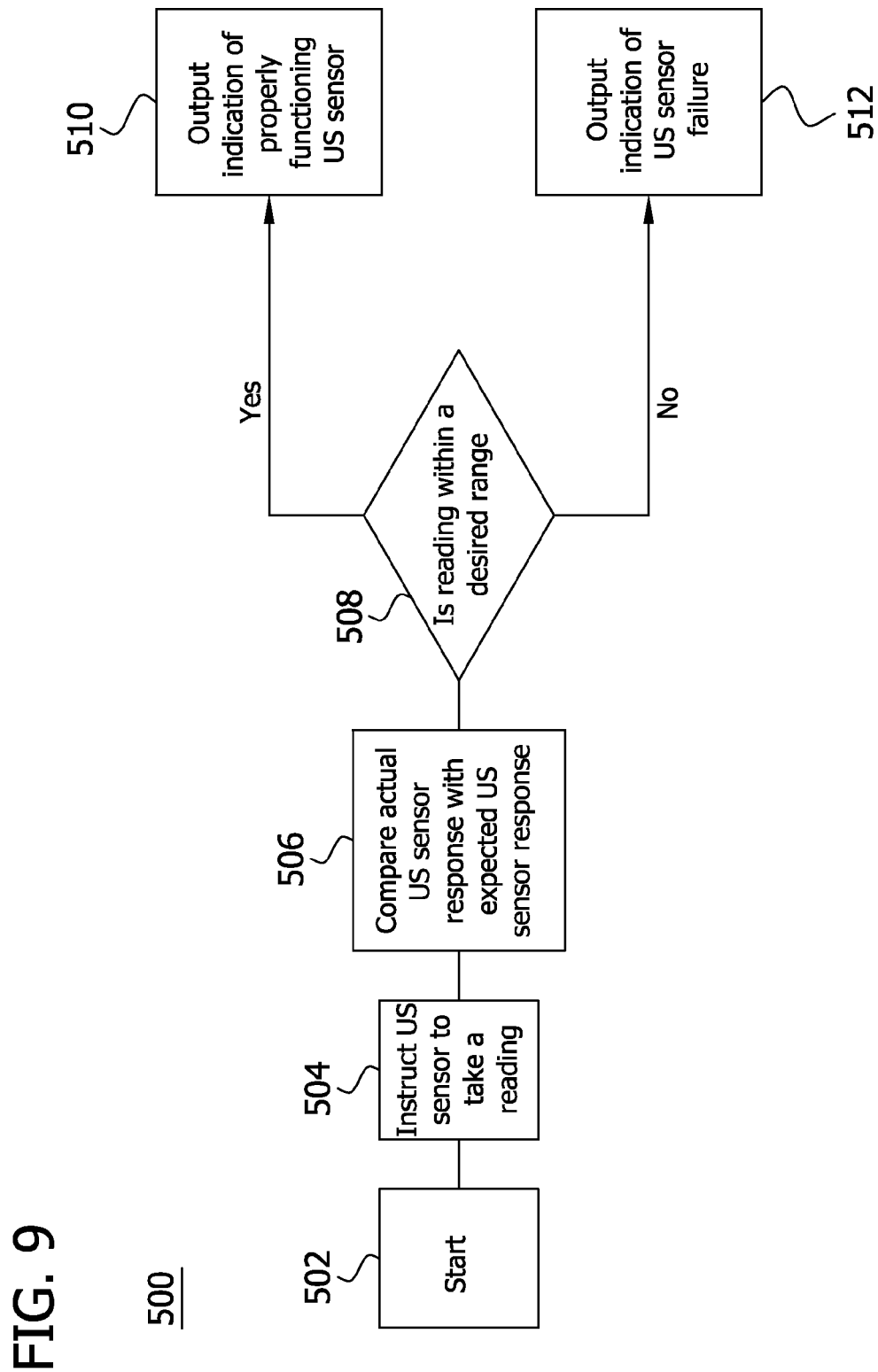
FIG. 9 is a flow chart illustrating the steps and decision points of an ultrasonic sensor certification routine of the certification system; and, FIG. 10 is a flow chart illustrating the steps and decision points of a motor certification routine of the certification system.

Turning now to FIG. 9, the steps and decision points of a routine 500 for determining that the ultrasonic sensor 32 of the pumping apparatus 1 is functioning within a predetermined operational range may be initiated by routine 300. At step 504, the software subsystem 36 instructs the ultrasonic sensor 32 to measure the ultrasonic sensor response to the body 120. It should be understood that if sensor 32 is always on, step 504 may only require the software subsystem to retrieve a measurement. As discussed above, the ultrasonic wave-transmissive post 124 is formed of a material operable to induce an expected ultrasonic sensor response when the ultrasonic sensor is functioning properly. As a result, the actual ultrasonic sensor response measured at step 504 can be compared to the expected ultrasonic sensor response stored in memory 39. If at step 508 the actual ultrasonic sensor response is within a desired range of the expected ultrasonic sensor response, the software subsystem 36 may output an indication of a properly functioning ultrasonic sensor on display 21 (step 510). If the actual response is not within a desired range of the expected response, the software subsystem 36 may output an indication of an improperly functioning ultrasonic sensor on display 21 (step 512).

Figure 10:
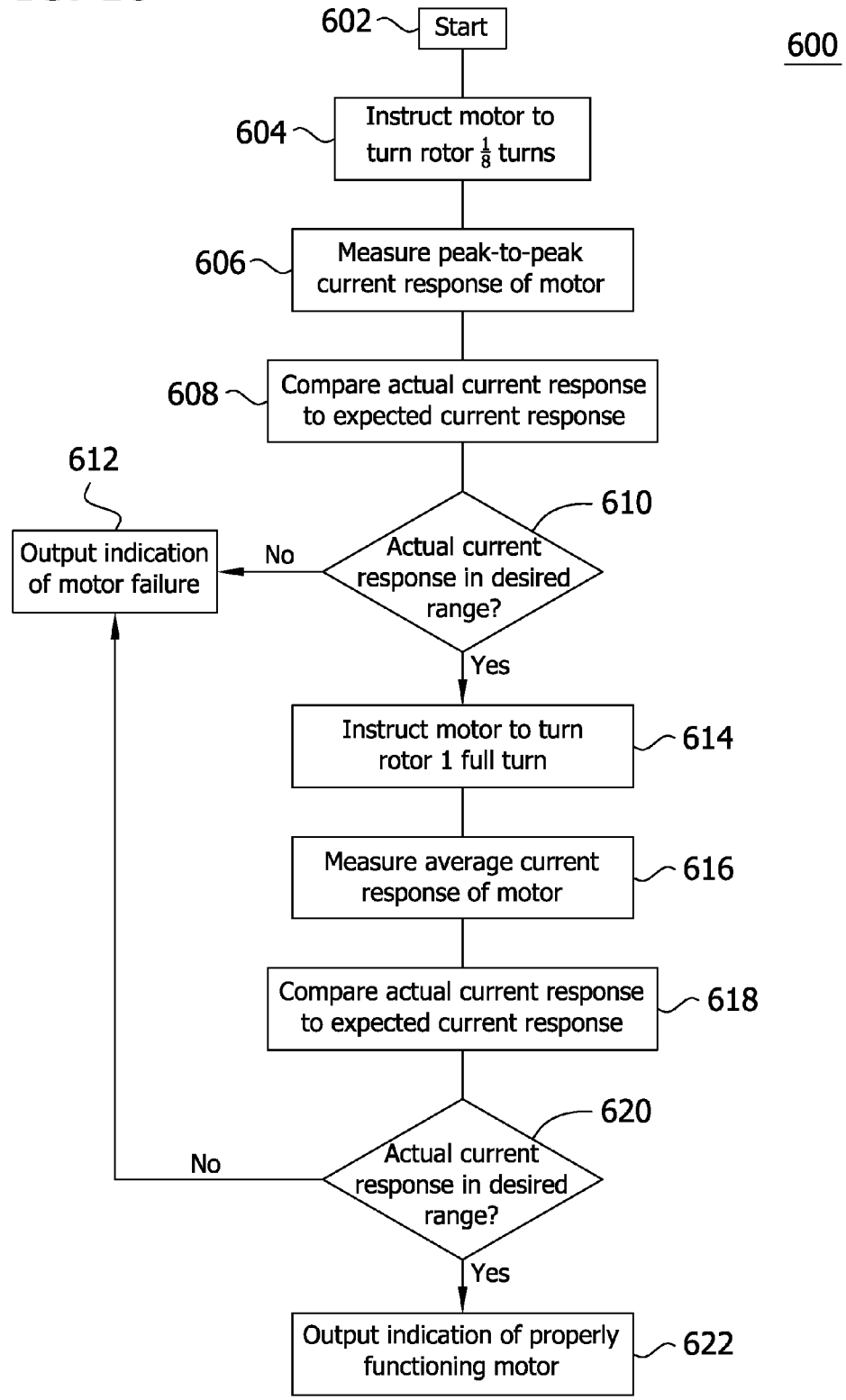

Turning now to FIG. 10, the steps and decision points of a routine 600 for determining that the motor 28 of the pumping apparatus 1 is functioning within a predetermined operational range may be initiated by routine 300. At step 604, the software subsystem 36 instructs the motor 28 to turn the rotor 29 one-eighth of one turn. At step 606, actual peak-to-peak current drawn by the motor 28 during the one-eighth turn of the rotor 29 is measured. The actual peak-to-peak current response may be compared to an expected peak-to-peak current response indicative of a properly functioning motor 28 at step 608. In the illustrated embodiment, if the reading is within a desired range of the expected peak-to-peak current response (step 610), the routine 600 will continue to step 614. If the actual response is not within a desired range of the expected response, the software subsystem 36 may output an indication of an improperly functioning motor 28 on display 21 at step 612. In other embodiments, where appropriate, the software subsystem may be configured to output an indication that peak-to-peak current response is within a desired range at step 610. In such embodiments, steps 614-624 may be performed in another routine.

In the illustrated embodiment, at step 614, the software subsystem 36 instructs the motor 28 to turn the rotor one full rotation. At step 618, the software subsystem 36 measures the actual average current drawn by the motor during the one full rotation. As discussed above, a properly functioning motor 28 under no load should produce an expected average current response during one full rotation. Thus, the actual average current response can be compared to the expected average current response during step 618. If the actual average current response is outside a desired range from the expected average current response (step 620), the software subsystem 36 may output a motor failure message to the display 21. If, however, the actual average current response is within the desired range from the expected average current response, the software subsystem 36 may output a message indicating that the motor 28 is functioning properly.

Accordingly, the certification system 36C works with the certification cassette 109 to determine whether at least one component of the pumping apparatus 10 is functioning within a predetermined operational range. The certification cassette 109 is arranged to align structures (e.g., the identification members 115A, 115B, the post 124, and the space 112) with components of the pumping apparatus 1 (e.g., the identification readers 17A, 17B, the ultrasonic sensor 32, and the motor 28) to test the performance of those components. It should be understood that, though the illustrated embodiment discusses a certification cassette having testing structures arranged for alignment with certain components of the illustrated pumping apparatus 1, other structures may be arranged within a certification cassette to test other components of other pumping apparatus embodiments without departing from the scope of the present invention.

Having described the invention in detail, it will be apparent that modifications and variations are possible without departing from the scope of the invention defined in the appended claims.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

The invention claimed is:

1. A certification cassette for testing a pumping apparatus including at least one identification reader, the cassette comprising:
   a housing configured for releasable attachment to the pumping apparatus in an aligned position;
   a body separate and distinct from the housing of the cassette and positioned in the housing;
   a space defined within the housing and configured to receive a rotor of the pumping apparatus therein when the housing is in the aligned position, the space being free of fluid carrying conduits disposed for engaging the rotor; and
   an identification member on the body and positioned in the housing, the identification member being operable to induce an expected identification reader response when the identification reader is functioning properly, the cassette configured to operatively align the identification member with the identification reader when the housing is in the aligned position.

2. The certification cassette of claim 1, wherein the identification member comprises identification member components disposed in different places on the housing.

3. The certification cassette of claim 2, wherein there is one distinct identification member component for each identification reader of the pumping apparatus.

4. The certification cassette of claim 1, wherein the identification member comprises one of a magnetic material and a magnetically-susceptible metallic material.

5. The certification cassette of claim 1, wherein the identification member is configured to induce an expected Hall-effect sensor response when the identification reader is functioning properly.

6. The certification cassette of claim 1, further comprising an ultrasonic wave-transmissive body supported by the housing, the body being configured to induce an expected ultrasonic sensor response when an ultrasonic sensor of the pumping apparatus is functioning properly.

7. The certification cassette of claim 6, wherein the cassette is configured to align the body with the ultrasonic sensor when the housing is in the aligned position.

8. A method of providing a certification cassette, comprising providing a certification cassette for testing a pumping apparatus, wherein the cassette has a housing configured for releasable attachment to the pumping apparatus in an aligned position; a space defined by the housing and configured to receive a rotor of the pumping apparatus therein when the housing is in the aligned position, wherein the space is free of fluid carrying conduits disposed for engaging the rotor; and a body separate and distinct from the housing of the cassette and positioned in the housing, the body comprising a post formed from an ultrasonic wave-transmissive material positioned in the housing, wherein the body is configured to induce an expected ultrasonic sensor response when the ultrasonic sensor is functioning properly, and wherein the cassette is arranged to align the body with the ultrasonic sensor when the housing is in the aligned position.

9. The method of claim 8, wherein the cassette further comprises an identification member positioned in the housing, the identification member operable to induce an expected identification reader response from an identification reader of the pumping apparatus when the identification reader is functioning properly, wherein the cassette is arranged to operatively align the identification member with the identification reader when the housing is in the aligned position.

10. A certification cassette for testing a pumping apparatus, the cassette comprising:
a housing configured for releasable attachment to the pumping apparatus in an aligned position;
a space defined by the housing and configured to receive a rotor of the pumping apparatus therein when the housing is in the aligned position, the space being free of fluid carrying conduits disposed for engaging the rotor; and,
a body separate and distinct from the housing of the cassette and positioned in the housing, the body comprising a post formed from an ultrasonic wave-transmissive material positioned in the housing, the body being configured to induce an expected ultrasonic sensor response when the ultrasonic sensor is functioning properly, the cassette being arranged to align the body with the ultrasonic sensor when the housing is in the aligned position.

11. The certification cassette of claim 10, wherein the ultrasonic wave-transmissive material has a density greater than air.

12. The certification cassette of claim 10, wherein the ultrasonic wave-transmissive material comprises silicone.

13. The certification cassette of claim 10, wherein the post has a cylindrical shape.

14. The certification cassette of claim 10, wherein the body is free of liquid.

15. The certification cassette of claim 10, further comprising an identification member positioned in the housing, the identification member operable to induce an expected identification reader response from an identification reader of the pumping apparatus when the identification reader is functioning properly.

16. The certification cassette of claim 15, wherein the cassette is arranged to operatively align the identification member with the identification reader when the housing is in the aligned position.

* * * * *